United States Patent [19]

Ippen et al.

[11] Patent Number: 4,581,453

[45] Date of Patent: Apr. 8, 1986

[54] GUANIDINOTHIAZOLE DERIVATIVES CONTAINING ALKYLENE BRIDGES, AND THEIR USE FOR INFLUENCING LIPID METABOLISM

[75] Inventors: Joachim Ippen, Cologne; Elisabeth Perzborn, Wuppertal; Walter Puls, Wuppertal; Klaus Schaller, Wuppertal; Friedel Seuter, Wuppertal, all of Fed. Rep. of Germany

[73] Assignee: Bayer Aktiengesellschaft, Leverkusen, Fed. Rep. of Germany

[21] Appl. No.: 492,776

[22] Filed: May 9, 1983

[30] Foreign Application Priority Data

May 28, 1982 [DE] Fed. Rep. of Germany ....... 3220118

[51] Int. Cl.$^4$ .................. C07D 239/02; A61K 31/495
[52] U.S. Cl. .................................. 544/331; 544/332; 548/183; 548/184; 548/185; 548/187; 548/190; 548/192; 514/272; 514/275; 514/369; 514/370; 514/371
[58] Field of Search ................ 544/331, 332; 424/251; 514/369, 370, 371, 272, 275; 548/183, 184, 185, 187, 190, 192

[56] References Cited

PUBLICATIONS

Usui, Ann. Rep. Takeda Res. Lab., 1968, 27, 96–111.
Hans Beyer et al, Chem. Abst., vol. 57, 4643–4644.
Boedeker et al, Chem. Abst., vol. 84, 59284h.
Nabih et al, J. of Pharmaceutical Science, vol. 61, No. 6, 1972, pp. 967–968.
Beyer et al, Liebigs Ann. Chem., 748 (1971) pp. 109–122.
Usi, Chem. Abst., vol. 70 (1969) 77845g.
Rembarz et al, Chem. Abst., vol. 100 (1984) 6463h.

*Primary Examiner*—Donald G. Daus
*Assistant Examiner*—Cecilia Shen
*Attorney, Agent, or Firm*—Sprung, Horn, Kramer & Woods

[57] ABSTRACT

The invention relates to guanidinothiazol derivatives of Formula (I) as defined herein, said compounds being useful for influencing lipid metabolism, as antithombotic agents and as antimycotic agents. Also included in the invention are compositions containing said guanidinothiazol derivatives of Formula (I) and the use of said compounds and compositions for treatment of the above-mentioned conditions. In addition, the invention includes methods for the manufacture of the guanidinothiazole derivatives of Formula (I).

15 Claims, No Drawings

GUANIDINOTHIAZOLE DERIVATIVES CONTAINING ALKYLENE BRIDGES, AND THEIR USE FOR INFLUENCING LIPID METABOLISM

The present invention relates to new guanidinothiazole derivatives containing alkylene bridges, a process for their preparation and their use as medicaments, in particular for influencing lipid metabolism, as antithrombotic agents and as antimycotic agents.

The present invention relates to guanidinothiazole derivatives containing alkylene bridges, of the general formula (I)

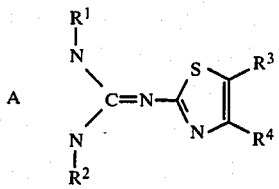

in their isomeric forms in which
A represents an alkylene radical an optionally substituted by aryl, alkyl, aralkyl, hydroxy,
$R^1$ and $R^2$ can be identical or different and represent hydrogen or optionally substituted alkyl,
$R^3$ represents hydrogen, optionally substituted alkyl, optionally substituted aryl, carbalkoxy, carbaryloxy or carboxamide and
$R^4$ represents hydrogen, optionally substituted alkyl, optionally substituted aralkyl, optionally substituted aryl, optionally substituted heteroaryl, e.g. furyl, pyridyl, thienyl, optionally substituted alkenyl, carbalkoxy, carbaryloxy, carbooxamide or the radical

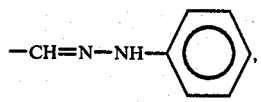

but $R^3$ and $R^4$ do not simultaneously denote hydrogen,
and their physiologically acceptable salts with inorganic and organic acids and bases.

The present invention preferably relates to guanidinothiazole derivatives containing alkylene bridges, of the above general formula (I), in which
A represents an optionally substituted alkylene radical with preferably 2 to 4 carbon atoms in the chain,
$R^1$ and $R^2$ can be identical or different and represent hydrogen or optionally substituted lower alkyl, preferably with 1 to 4 C atoms,
$R^3$ represents hydrogen, or represents alkyl with 1–4 carbon atoms which is optionally substituted by hydroxyl, alkoxy, alkylthio, lower alkylcarbonyloxy or carbalkoxy, or represents aryl, in particular phenyl, the phenyl radical being optionally monosubstituted, disubstituted or polysubstituted by identical or different substituents from the group comprising alkyl with 1–4 carbon atoms, halogen, hydroxyl, alkoxy, alkylthio, amino and nitro, or represents carbalkoxy, in particular carbomethoxy, carbethoxy or carbocyclohexyloxy, or represents carbaryloxy, for example carbophenoxy, or represents carboxamide, in particular carboxamide in which the amide group is substituted by optionally substituted aryl or alkyl with 1–20 carbon atoms, and
$R^4$ represents hydrogen, or represents straight-chain, branched or cyclic alkyl with 1–10 carbon atoms which is optionally substituted by hydroxyl, alkoxy, alkylthio, optionally substituted aryloxy or arylthio, halogen, carbalkoxy, carboxamide or cyano, or represents aryl, in particular phenyl, biphenyl, naphthyl, tetrahydronaphthyl or indanyl, which is optionally monosubstituted or polysubstituted by identical or different substituents from the group comprising straight-chain, branched or cyclic alkyl with 1–10 carbon atoms, hydroxyl, alkoxy, halogen, amino and nitro, or represents heteroaryl, in particular optionally substituted furyl or thienyl, or represents alkenyl which is optionally substituted by lower alkyl, aryl or carbalkoxy, or represents carbalkoxy, in particular carbalkoxy in which the alkoxy group contains a straight-chain, branched or cyclic alkyl radical with 1–10 carbon atoms, or represents carbaryloxy, in particular carbophenoxy, or represents carboxamide, in particular carboxamide in which the amide group is substituted by optionally substituted aryl or alkyl with 1–20 carbon atoms, and their physiologically acceptable salts with inorganic and organic acids and bases.

As used herein and unless otherwise specified the term "alkyl", (taken either per se or as a portion of a moiety, e.g., "alkoxy", "alkylthio", "carboalkoxy", etc.) refers preferably to groupings containing 1 to 10, especially 1 to 4 and particularly 1 or 2 carbon atoms; the term "aryl" (taken either per se or as a portion of a moiety, e.g. "aralkyl") refers preferably to mono- or bi-cyclic carbocyclic aryl; the term "heteroaryl" refers preferably to groupings containing oxygen, nitrogen or sulfur atoms as hetero atoms, such as pyridine, thiophane, etc.; the term "alkenyl" preferably contains up to 8 and particularly up to 3 or 4 carbon atoms; the term "halogen" preferably refers to chlorine, bromine or fluorine; the term "cycloalkyl" preferably refers to cycloalkyl having 3 to 7 ring members, preferably cyclopentyl and cyclohexyl.

Very particularly preferred guanidinothiazole derivatives containing alkylene bridges, of the above formula (I) are those which are listed in Table (I) and have the substituents shown in Table (I).

The guanidinothiazole derivatives according to the invention, which contain alkylene bridges and are of the formula (I), are synthesised in accordance with the following equations:

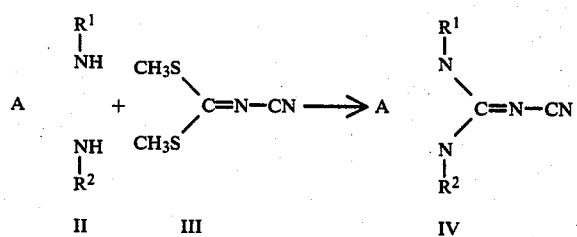

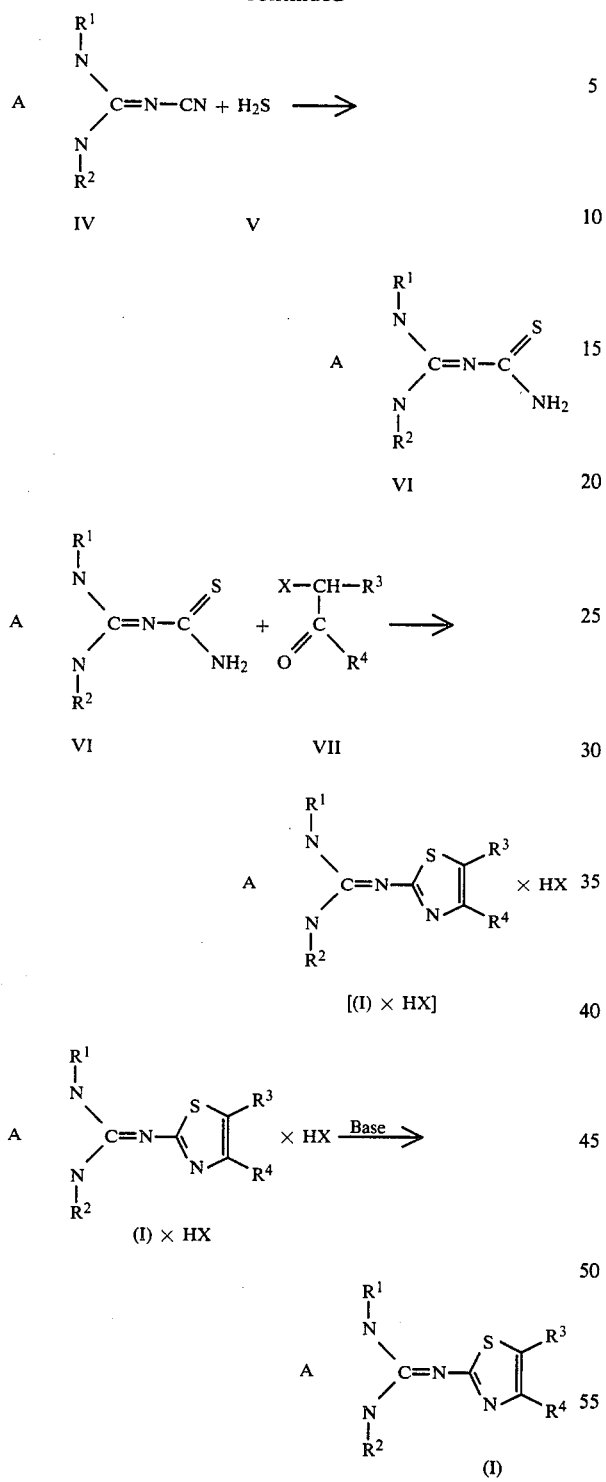

(II) with S,S$^1$-dimethyl N-cyanoimidodithiocarbonate (III).

Guanylthiourea is obtained by addition of hydrogen sulphide onto N-cyanoguanidine [compare Org. Synth. Coll. Volume IV, 502]. The guanylthioureas containing N,N$^1$-alkylene bridges (VI) are obtained in an analogous manner from the cyclic N-cyanoguanidines (IV). The solvents used in this reaction are water and protic and aprotic organic solvents, for example ethanol, dimethylformamide or pyridine, and mixtures of the solvents. The reaction is carried out at a temperature of 0°–150° C., preferably at 20°–120° C.

The reaction of α-halogenoketones with thiocarboxamides to give 1,3-thiazoles is known in principle [compare C. Ferri, Reaktionen der organischen Synthese (Reactions in Organic Synthesis), Thieme Verlag, Stuttgart 1978, page 731]. The guanidinothiazole derivatives, containing alkylene bridges, [(I)xHX.] or (I) according to the invention are obtained by reaction of the guanylthioureas containing N,N$^1$-alkylene bridges (VI) with α-halogeno-ketones or aldehydes (VII).

Diluents which are used in this reaction are organic solvents and water. Preferred solvents are water, aromatic and heteroaromatic hydrocarbons, of which toluene and pyridine are particularly preferred, ketones, for example acetone, and alcohols, for example ethanol.

The reaction temperatures can be varied within a substantial range. The reaction is generally carried out between about 0° C. and 180° C., preferably between room temperature and the boiling point of the particular diluent.

The reaction time depends on the temperature and the diluent and is between 0.5 and 24 hours.

The free guanidinothiazole derivatives containing alkylene bridges (I) can be liberated from the salts of the compounds [(I)xHX] according to the invention with bases. Alkali metal and alkaline earth metal carbonates, bicarbonates and hydroxides and ammonia and organic bases, such as tertiary aliphatic and aromatic amines, are preferably used. Water is preferably employed as the diluent.

It is clear that, providing R$^1$ and R$^2$ denote hydrogen, the guanidinothiazole derivatives containing alkylene bridges, of the general formula (I), can also be in the form of double-bond isomers, which are shown by the formulae (Ia) and (Ib). These isomerism possibilities may also occur in the particular precursors. The present invention also includes the isomeric forms Ia and Ib of the formula I.

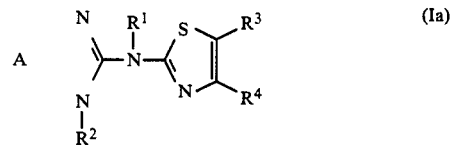

(Ia)

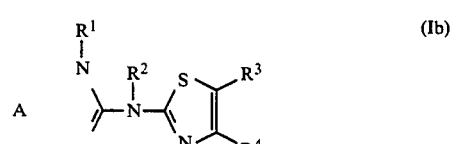

(Ib)

The terms such as A, R$^1$, R$^2$, R$^3$ and R$^4$ given in the equations have the abovementioned meaning; X denotes hydroxyl or halogen, preferably chlorine or bromine.

The cyclic N-cyanoguanidines of the general formula (IV) are obtained in a manner which is in itself known [compare C. M. Baltzer and C. G. MacCarty, J. Org. Chem. 38, 155 (1973); DT-OS (German Published Specification) No. 2,205,745] by reacting alkylenediamines Particularly preferred new active compounds are the compounds of formula I specifically listed in Table 1, which active compounds are prepared using procedures analogous to those described infra under "Preparation examples".

TABLE I

| Example | A | R¹ | R² | R³ | R⁴ | HX | Reaction conditions diluent temperature/time | Yield | Melting point | Preparation of the free compounds from the salts |
|---|---|---|---|---|---|---|---|---|---|---|
| 1 | —(CH₂)₂— | H | H | H | —CH₃ | HCl | acetone, reflux 8 hours | 92% | 281–283° C. | |
| 2 | —(CH₂)₂— | H | H | H | —CH₂Cl | HCl | acetone, room temperature 10 hours | 91% | 228–230° C. | |
| 3 | —(CH₂)₂— | H | H | H | —CH₂CO₂C₂H₅ | — | acetone, reflux 5 hours | 29% | 124–125° C. | NaHO₃, H₂O |
| 4 | —(CH₂)₂— | H | H | H | (tetrahydronaphthyl-CH₃) | — | acetone, reflux 2 hours | 15% | 228–230° C. | NaOH, H₂O |
| 5 | —(CH₂)₂— | H | H | H | (Cl, CH₃-phenyl) | — | acetone, reflux 4 hours | 34% | 230–231° C. | NaOH, H₂O |
| 6 | —(CH₂)₂— | H | H | H | (biphenyl) | — | acetone, reflux 4 hours | 44% | 279–280° C. | NH₃, H₂O |
| 7 | —(CH₂)₂— | H | H | H | (OCH₃-phenyl) | — | acetone, reflux 2 hours | 33% | 260–261° C. | — |
| 8 | —(CH₂)₂— | H | H | H | H | H₂O | water, room temperature 3 hours | 25% | 117–118° C. | NH₃, H₂O |
| 9 | —(CH₂)₃— | H | H | H | —CH₃ | HCl | acetone, room temperature 8 hours | 90% | 250–251° C. | |
| 10 | —(CH₂)₃— | H | H | H | —C(CH₃)₃ | HCl | acetone, reflux 10 hours | 92% | 199–201° C. | |
| 11 | —(CH₂)₃— | H | H | H | —CH₂Cl | HCl | acetone, reflux 2 hours | 72% | 221–223° C. (decomposition) | |
| 12 | —(CH₂)₃— | H | H | H | —CH₂—S—C(=NH)NH₂ | 2HCl | | 71% | 228–238° C. | |
| 13 | —(CH₂)₃— | H | H | H | —CH₂—CO₂C₂H₅ | — | acetone, reflux 5 hours | 41% | 168–169° C. | NaHCO₃, H₂O |
| 14 | —(CH₂)₃— | H | H | —CO₂C₂H₅ | —CH₃ | — | acetone, reflux 2 hours | 22% | 185–186° C. | NaHCO₃·H₂O |

TABLE I-continued

| Example | A | $R^1$ | $R^2$ | $R^3$ | $R^4$ | HX | Reaction conditions diluent temperature/time | Yield | Melting point | Preparation of the free compounds from the salts |
|---|---|---|---|---|---|---|---|---|---|---|
| 15 | $-(CH_2)_3-$ | H | H | $-CO_2-$ | $-CH_3$ | — | acetone, reflux 4 hours | 27% | 187–188° C. | NaHCO$_3$, H$_2$O |
| 16 | $-(CH_2)_3-$ | H | H | $-(CH_2)_2-OAC$ | $-CH_3$ | HCl | acetone, reflux 10 hours | 8% | 230–231° C. | |
| 17 | $-(CH_2)_3-$ | H | H | $-CO-NH-$ | $-CH_3$ | HCl | acetone, reflux 1 hour | 92% | 289–290° C. | |
| 18 | $-(CH_2)_3-$ | H | H | H | $-CH_2-O-$ | — | | 9% | 185–187° C. | |
| 19 | $-(CH_2)_3-$ | H | H | H | $-CH_2-S-$ | — | | 46% | 139–143° C. | |
| 20 | $-(CH_2)_3-$ | H | H | H | 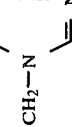$-CH_2-N$ | — | | 29% | 163–164° C. | |
| 21 | $-(CH_2)_3-$ | H | H | H | 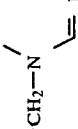$-CH_2-N$ | — | | 19% | 206–208° C. | |
| 22 | $-(CH_2)_3-$ | H | H | H |  | HCl | acetone, reflux 1 hour | 90% | 244–245° C. | |
| 23 | $-(CH_2)_3-$ | H | H | H |  | — | acetone, reflux 2 hours | 42% | 270–272° C. | NaOCH$_3$ C$_2$H$_5$OH |
| 24 | $-(CH_2)_3-$ | H | H | H |  | — | acetone, reflux 2 hours | 49% | 223–228° C. | H$_2$O, NaHCO$_3$ |

TABLE I-continued

| Example | A | $R^1$ | $R^2$ | $R^3$ | $R^4$ | HX | Reaction conditions diluent temperature/time | Yield | Melting point | Preparation of the free compounds from the salts |
|---|---|---|---|---|---|---|---|---|---|---|
| 25 | $-(CH_2)_3-$ | H | H | H | 6-methyl-1,2,3,4-tetrahydronaphthalen-2-yl | HCl | acetone, reflux 2 hours | 66% | 230–232° C. | |
| 26 | $-(CH_2)_3-$ | H | H | H | 5-methyl-indan-2-yl | HCl | $C_2H_5OH$, reflux 2 hours | 75% | 234–236° C. | |
| 27 | $-(CH_2)_3-$ | H | H | H | 2,5-dichloro-4-methylphenyl | HCl | acetone, reflux 3 hours | 77% | 255–257° C. | |
| 28 | $-(CH_2)_3-$ | H | H | H | 4-methyl-4'-biphenylyl | HCl | acetone, reflux 2 hours | 70% | 232–233° C. | |
| 29 | $-(CH_2)_3-$ | H | H | H | 4'-chloro-4-methylbiphenylyl | HCl | acetone, reflux 3.5 hours | 13% | 279–281° C. (decomposition) | |
| 30 | $-(CH_2)_3-$ | H | H | H | 5-chloro-2-methoxy-4-methylphenyl | HCl | acetone, reflux 2 hours | 43% | 236–237° C. | |
| 31 | $-(CH_2)_3-$ | H | H | H | 4-hydroxy-3-methylphenyl | HCl | acetone, reflux 4 hours | 89% | 280–283° C. | |
| 32 | $-(CH_2)_3-$ | H | H | H | 4-methoxy-3-methylphenyl | HCl | acetone, reflux 4 hours | 63% | 224–225° C. | |
| 33 | $-(CH_2)_3-$ | H | H | H | 5-chloro-2,3-dimethylphenyl | HCl | acetone, reflux 2 hours | 81% | 242–244° C. | |
| 34 | $-(CH_2)_3-$ | H | H | H | 2',4'-dichloro-4-methylbiphenylyl | HCl | acetone, reflux 2 hours | 66% | 208–210° C. | |

TABLE I-continued

| Example | A | $R^1$ | $R^2$ | $R^3$ | $R^4$ | HX | Reaction conditions diluent temperature/time | Yield | Melting point | Preparation of the free compounds from the salts |
|---|---|---|---|---|---|---|---|---|---|---|
| 35 | —(CH$_2$)$_3$— | H | H | H | 4-Cl-C$_6$H$_4$ | HBr | acetone, reflux 2 hours | 77% | 263–265° C. | |
| 36 | —(CH$_2$)$_3$— | H | H | H | 4-NO$_2$-C$_6$H$_4$ | HBr | acetone, reflux 2 hours | 97% | 308–309° C. (decomposition) | |
| 37 | —(CH$_2$)$_3$— | H | H | H | 2-OCH$_3$, 4-OH, 5-CH$_3$ phenyl | — | pyridine, reflux 2 hours | 63% | 210–211° C. | |
| 38 | —(CH$_2$)$_3$— | H | H | H | (3,5-dibromo-coumarin-8-yl-methylene)-methyl | — | acetone, reflux 1.5 hours | 16% | >320° C. | H$_2$O, NaOH |
| 39 | —(CH$_2$)$_3$— | H | H | H | nitrofuryl-methylene-methyl | — | acetone, reflux 1 hour | 92% | >310° C. | |
| 40 | —(CH$_2$)$_3$— | H | H | H | (2,6-dichloro-α-ethoxycarbonyl-styryl)-methyl | — | acetone, reflux 3 hours | 59% | 225–226° C. | H$_2$O, NH$_3$ |
| 41 | —(CH$_2$)$_3$— | H | H | —CH$_3$ | —CH=N—NH—C$_6$H$_5$ | — | acetone, reflux 5 hours | 17% | 232–236° C. | H$_2$O, NaHCO$_3$ |
| 42 | —(CH$_2$)$_3$— | H | H | H | 3,5-diethyl-4-methyl-hydroxyphenyl | HCl | acetone, reflux 2 hours | 71% | 236–238° C. | |

TABLE I-continued

| Example | A | R¹ | R² | R³ | R⁴ | HX | Reaction conditions diluent temperature/time | Yield | Melting point | Preparation of the free compounds from the salts |
|---|---|---|---|---|---|---|---|---|---|---|
| 43 | —(CH₂)₃— | H | H | H | 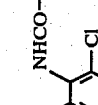 (2-methyl-5-chlorophenol) | — | pyridine, reflux 3 hours | 90% | >320° C. | |
| 44 | —(CH₂)₃— | H | H | H | 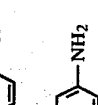 (2-methyl-3-NHCO—CH₃-6-chlorophenyl) | — | acetone, reflux 2 hours | 19% | 275–277° C. | H₂O, NaHCO₃ |
| 45 | —(CH₂)₃— | H | H | H | 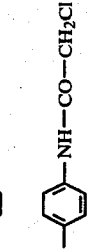 (4-NH₂-phenyl) | — | acetone, reflux 2 hours | 55% | 238–240° C. | H₂O, NaHCO₃ |
| 46 | —(CH₂)₃— | H | H | H |  (4-NH—CO—CH₂Cl-phenyl) | HCl | acetone, reflux 2 hours | 55% | 241° C. decomposition | |
| 47 | —(CH₂)₃— | H | H |  (phenyl) | phenyl | — | pyridine, reflux 4 hours | 54% | 249–250° C. | |
| 48 | —(CH₂)₃— | H | CH₃ | H | —CH₃ | — | acetone, reflux 2 hours | 73% | 90–91° C. | H₂O, NaOH |
| 49 | —(CH₂)₃— | H | CH₃ | H | 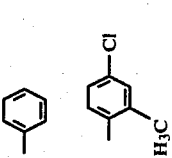 (phenyl) | HCl | acetone, reflux 2 hours | 95% | 282–283° C. | |
| 50 | —(CH₂)₃— | H | CH₃ | H |  (3-chlorophenyl) | HCl | acetone, reflux 1 hour | 45% | 215–216° C. | |
| 51 | —(CH₂)₃— | H | CH₃ | H | 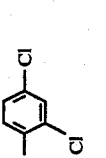 (2-methyl-4,5-dichlorophenyl) | HCl | acetone, reflux 1 hour | 68% | 247–249° C. | |
| 52 | —(CH₂)₄— | H | H | H | —CH₃ | HCl | acetone, reflux 2 hours | 53% | 185–187° C. | |
| 53 | —(CH₂)₄— | H | H | H |  (phenyl) | HCl | acetone, reflux 2 hours | 78% | 235–237° C. | |

TABLE I-continued

| Example | A | R¹ | R² | R³ | R⁴ | HX | Reaction conditions diluent temperature/time | Yield | Melting point | Preparation of the free compounds from the salts |
|---|---|---|---|---|---|---|---|---|---|---|
| 54 | —(CH₂)₄— | H | H | H | 3-Cl-4-CH₃ cyclohexenyl (H₃C, Cl substituted) | HCl | acetone, reflux 2 hours | 66% | 196–197° C. | |
| 55 | —(CH₂)₄— | H | H | H | 2,4-diCl-phenyl | HCl | acetone, reflux 2 hours | 77% | 228–230° C. | |
| 56 | —(CH₂)₃— | H | H | H | p-tolyl-NH—C(=N—CN)—NHCH₃ | — | | 49% | 283–285° C. | |
| 57 | —(CH₂)₃— | H | H | H | p-tolyl-NH—C(=N—CN)—NH—CH₂—C₆H₅ | — | | 42% | 236–237° C. | |
| 58 | —(CH₂)₃— | H | H | H | adamantyl | — | acetone, pyridine 3 hours reflux | 52% | 257–258° C. | H₂O, NH₃ |
| 59 | —(CH₂)₃— | H | H | H | p-tolyl-NH—C(=N—CN)—SCH₃ | — | | 56% | >310° C. | |
| 60 | C₆H₅—CH—CH— / —CH— | H | H | H | phenyl | — | acetone, reflux 8 hours | 35% | 253–255° C. | H₂O DMSO NH₃ |
| 61 | H₃C—C(CH₂—C₆H₅)(CH₂—)—CH₂— | H | H | H | —CH₃ | — | acetone, reflux 5 hours | 51% | 160–161° C. | H₂O, NH₃ |
| 62 | H₅C₆—H₂C—C(CH₂—C₆H₅)(CH₂—)—CH₂— | H | H | H | phenyl | 2 × H₂O | acetone, reflux 10 hours | 77% | 223–225° C. | DMSO H₂O NaOH |
| 63 | —CH₂—CH(OH)—CH₂— | H | H | H | phenyl | — | acetone, reflux 5 hours | 96% | 219–220° C. | H₂O, NH₃ |

The compounds of Examples 18, 19, 20 and 21 in Table I can be prepared from the compound of Example 11 by reaction with corresponding nucleophiles, such as 2,4-dichlorophenol, thiophenol, imidazole and triazole.

The substance Examples 56 and 57 can also be obtained starting from the compound of Example 45 by reaction with, for example,

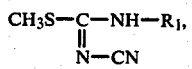

wherein $R^1$ denotes alkyl or aryl.

The biological action of the compounds prepared according to the invention has been demonstrated by the following experiments:

Platelet aggregation-inhibiting action

The use of platelet aggregation-inhibiting medicaments as antithrombotic agents can meanwhile be regarded as a recognised therapy principle. The participation of platelets in atherosclerotic processes is also known, so that substances which have these properties and are to be used in the said indications are to be evaluated as advantageous.

Blood from healthy subjects of both sexes was used in the in vitro experiments. One part of 3.8% strength aqueous sodium citrate solution was mixed, as an anticoagulant, with 9 parts of blood. Platelet-rich citrate plasma (PRP) is obtained from this blood by means of centrifugation (Jurgens/Beller: Klinische Methoden der Blutgerinnungsanalyse [Clinical Methods of Blood Coagulation Analysis]; Thieme-Verlag Stuttgart 1959).

For the in vitro experiments, the minimum effective active compound concentration which inhibits platelet aggregation in the corresponding PRP samples is given. For these investigations, 0.8 ml of PRP and 0.1 ml of the active compound solution were pre-incubated in a water bath at 37° C. The platelet aggregation was then determined by the turbidometric method (Born, G. V. R.: J. Physiol. 162, 67, 1962) in an aggregometer at 37° C. (Seuter, F.: Haemostasis 5, 85–95, 1976). For this, 0.1 ml of an aggregation-inducing collagen suspension was added to the pre-incubated sample.

The change in optical density of the sample of PRP was recorded over a period of 6 minutes and was determined via the reading after 6 minutes. The percentage inhibition is calculated from the corresponding readings. Moreover, the platelet aggregation was also determined in the context of the thromboatherosclerosis experiment. In carrying out these experiments, the active substance was administered to the animals orally in a Tylose suspension over a period of 10 days. On the 10th day, the animals were exsanguinated 90 minutes after the oral administration of the substance, and the PRP was isolated by means of centrifugation. After the PRP has been isolated, in vitro measurement of the aggregation inhibition starts, analogously to the process which has been described for the in vitro experiments; but without pre-incubation of the samples. 3 parts of rat PRP were also diluted with one part of physiological saline solution.

Anti-atherosclerotic action

In the Western industrial countries, heart and vascular diseases lead the mortality statistics, accounting for >50% of the cases of death. The practical and social significance is demonstrated by the frequency and severity of diseases, which to a high degree affect people at the peak of their performance. In the arterial part of the vascular system, the diseases are in most cases chronic disease processes, predominantly arteriosclerotic changes, which usually lead to partial or complete blockage of the vessels. The tissue damage caused by restricted circulation can lead as far as local tissue death or infarction (heart, brain). Coronary sclerosis, for example, is the focal point of infarction pathogenesis.

Arteriosclerosis, or atherosclerosis in the narrower sense, is a very complex disease in which it is possible to observe the participation of at least 3 main processes: 1. vascular wall damage with subsequent proliferation of its smooth muscle cells and formation of a fibromusculoelastic lesion; 2. lipid deposits; 3. mural clot formation and deposition thereof in the vascular wall. In the past, varying significance has been placed on these factors, which has led to the "thrombogenic" and "lipid infiltration" theory.

In our experiment, both factors were taken into consideration, but vascular wall damage with subsequent proliferation of the intima stands in the foreground. These processes have recently been regarded by many authors as the most significant in the aetiopathogenesis of arteriosclerosis.

Because of some fluid transitions between atherosclerosis and thrombosis, we have called the method used "thromboatherosclerosis model".

Method

Literature: Seuter, F., Sitt, R. and Busse, W. D., Experimentally induced thromboatherosclerosis. Folia angiologica 28, 85 (1980).

Atherosclerotic plaques are induced in rats by combination of two noxae (risk factors), that is to say vascular lesion and hyperlipaemia. By supercooling of the arteria carotis comm. (2 minutes, −10° C.), partial or complete endothelial scaling occurs in a locally restricted area. Proliferation of the intima occurs within 10 days, which is a relatively short period for such experiments, and largely corresponds to the early stages of atherosclerotic plaques in humans. The proliferation zones are removed and weighed. The moist weight in the supercooled segment of 1 cm is about 200–300 μg. The animals are additionally given a high-fat diet having the following composition:

3% of cholesterol
1% of Na cholate
34% of sucrose
10% of lard
52% of normal feed (Altromin ®).

The lipid deposits are stained with the fat-soluble dyestuff Sudan IV and can be determined as an additional parameter.

In addition to alkylating cytostatic agents and glucocorticoids, which inhibit cell proliferation nonspecifically, only heparin has hitherto been effective in this model following parenteral administration. Lipid-lowering substances, such as cholestyramine, neomycin, nicotinic acid and the like were ineffective. The dose-dependent action of heparin, which serves as a positive reference standard in all experiments, has been described (Sitt, R., Seuter, F. and Busse, W. D., Suppression by Heparin of intimal proliferation in the injured carotid artery (rat). Arch Pharmacol., Suppl. 311, Abstr. 188, 1980).

Surprisingly, compounds from the chemical substance class of guanidinothiazole derivatives with alkylene bridges had an antiatherosclerotic action following oral administration, in that the formation of a myointimal plaque (proliferation of the intima) was inhibited (table).

Arachidonic acid metabolism

The knowledge that a number of metabolites of arachidonic acid are significant for the aetiology, pathogenesis and manifestation of coronary diseases, such as Angina pectoris (prince's metal), cardiac infarction, diseases of the peripheral vessels and arteriosclerosis, has meant that pharmacological influencing of arachidonic acid metabolism has become an important starting point in the therapy of circulatory diseases.

Individual metabolites of very potent regulators of the vascular functions, and moreover have considerable significance in the formation of thromo-embolisms and pathological changes of the vascular wall.

The physiological or pathophysiological significance of pharmacological intervention in arachidonic acid metabolism is influenced decisively by the nature and site of the intervention in the arachidonic acid metabolism. In very simple terms, the relationships can be shown, for example, as follows:

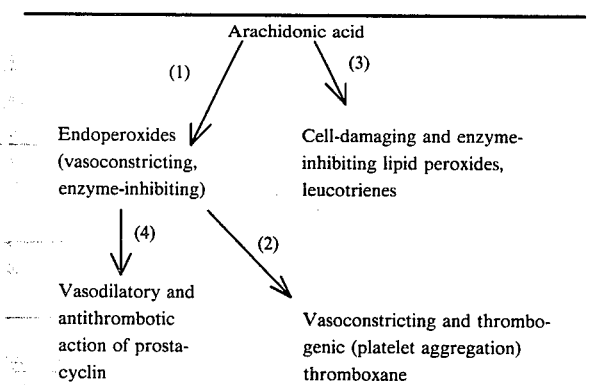

(1) = cyclooxygenase inhibitors which suppress the formation of endoperoxides and thus of thromboxane
(2) = thromboxane synthetase inhibitors
(3) = lipoxygenase inhibitors
(4) = prostacyclin stimulators The scheme clearly shows that the therapy of vascular diseases by intervention in arachidonic acid metabolism can be carried out particularly effectively by substances which do not intervene only at one site in the metabolism of arachidonic acid, but have a profile of inhibiting or promoting effects on the individual metabolism steps.

The lipid peroxides formed by the lipoxygenase degradation route are of importance in inflammation reactions. However, there are indications that these peroxides also participate in the formation of thromboses and the causing of endothelial damage. A blockade in the lipoxygenase path of the arachidonic acid metabolism could accordingly be a further desirable property.

Certain lipid peroxides, such as HPETE, generally have a cell-damaging action and appear to cause (irreversible) contractures of smooth muscle cells (vessels).

Method

In human platelets, $^3$H-arachidonic acid is converted into the products of the cyclooxygenase/thromboxane synthetase path, in particular thromboxane $A_2$, and those of the lipoxygenase path, HETE. Separation of the resulting products by thin layer chromatography gives a characteristic pattern. Inhibitors of the individual enzymatic reactions modify this pattern in a typical manner (Bailey, J. M. et al., Prostaglandins 13, 479–492 (1977)). The action of the compounds according to the invention on individual reactions in arachidonic acid metabolism are shown in Table 2.

On the basis of the effective qualities mentioned, the compounds according to the invention are suitable, for example, for treating or preventing cardiac infarctions, angina pectoris, thromboembolic diseases in the venous and arterial region (postoperatively, transitorially ischaemic attacks, amaurosis fugax and the like) and other vascular syndromes, such as arteriosclerosis.

| | Table of actions | |
|---|---|---|
| Example | Biological action | Activity, $ED_{50}$ (dose/concentration range) |
| 13 | PAH in vitro | $1 \times 10^{-4} - 1 \times 10^{-5}$ g/ml |
| 15 | Cyclooxygenase inhibition | $1 \times 10^{-5} - 3 \times 10^{-6}$ g/ml |
| 16 | PAH in vitro | $1 \times 10^{-4} - 1 \times 10^{-5}$ g/ml |
| 17 | PAH ex vivo (atherosclerosis experiment) | 100 mg/kg per orally |
| 25 | PAH ex vivo | 100 mg/kg per orally |
| 49 | (a) anti-atherosclerotic | 100 mg/kg per orally |
| | (b) PAH ex vivo | 100 mg/kg per orally |
| | (c) cyclooxgenase inhibition | $1 \times 10^{-5}$ g/ml |
| 53 | PAH in vitro | $1 \times 10^{-4} - 1 \times 10^{-5}$ g/ml |

PAH = platelet aggregation-inhibition

Antimycotic action

The guanidinothiazoles, with alkylene bridges, according to the invention display a surprising antifungal action against dermatophytes, yeasts and moulds.

Compared with the competing products "ketoconazol" and "doconazol", the substances claimed exhibit, in vitro, an inhibiting action (minimum inhibitory concentration) which is comparable, and even better against selected germs.

Antimycetic in vitro activity

Description of the experiment:

The in vitro tests were carried out in a series dilution test using germ inocula of on average $5 \times 10^4$ germs/ml of substrate. The nutrient medium used was (a) Sabourands' milieu d'épreuve for dermatophytes and moulds; and
(b) meat extract/dextrose broth for yeasts.

The incubation temperature was 20° C. and the incubation time was 24 to 96 hours for yeasts and 96 hours for dermatophytes and moulds.

The surprising action of the substance group according to the invention may be documented, for example, by the following test results:

| | Minimum inhibitory concentration (mcg/ml) | | | | |
|---|---|---|---|---|---|
| Example | Trichophyton mentagrophytes | Microsporum canis | Candida albicans | Torulopsis glabrata | Aspergillus fumigatus |
| 22 | <1 | <1 | 4 | 32 | <1 |
| 24 | <1 | <1 | 2 | 8 | <1 |
| 27 | <1 | <1 | <1 | 16 | 8 |

-continued

| | Minimum inhibitory concentration (mcg/ml) | | | | |
|---|---|---|---|---|---|
| Example | Trichophyton mentagrophytes | Microsporum canis | Candida albicans | Torulopsis glabrata | Aspergillus fumigatus |
| 33 | 2 | 2 | 2 | 16 | 2 |
| Ketoconazol | <1 | 4 | <1 | 1 | 16 |
| Doconazol | <1 | 8 | <1 | <1 | 4 |

Cholesterol loading

Cholesterol loading tests were carried out on conscious male or female Wistar rats weighing between 130–230 g.

Cholesterol and the substance to be tested were simultaneously administered orally in 0.75% strength tragacanth suspension. After 24 hours, the animals were sacrificed and the cholesterol content of the liver was determined. Cholesterol was determined by the Liebermann-Burchard method using the test combination of Boehringer Mannheim. Control animals received a corresponding volume of cholesterol/tragacanth suspension without the test substance. To monitor the rise in cholesterol as a result of cholesterol loading, tragacanth suspension containing no cholesterol was administered orally to another control group.

The surprising action of the substance group according to the invention may be documented, for example, by the following test results:

| Example No. | Dose (mg/kg) per orally | Reduction in the increase in liver cholesterol in percent in comparison with the control, following oral cholesterol loading |
|---|---|---|
| 17 | 100 | 56.1% |
| 25 | 10 | 65.3% |
|    | 30 | 78.1% |

It is to be described as decidedly surprising that the compounds according to the invention have these new and advantageous actions. As a novel substance class for the treatment of metabolism disorders, at the same time coupled with a very good tolerance, they represent an enrichment of pharmacy.

PREPARATION EXAMPLES

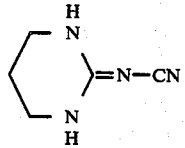

(a)

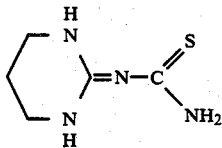

(b)

2-(N-Thiocarbamoylimino)-hexahydropyrimidine (b)

Hydrogen sulphide is first passed into a solution of 190 g (1.53 mols) of 2-(N-cyanimino)-hexahydropyrimidine (a) in 760 ml of water at 75° C. for 12 hours; and then at 65°–70° C. for another 25–30 hours. (On the second day, some of the precipitate no longer dissolves). The suspension is then warmed to 45° C. and 46 ml of 40% strength NaOH are added. Stirring is continued for 30 minutes and the residue is ground and filtered off with suction. After drying, 228 g (94%) of product are obtained. Melting point=187°–189° C. (decomposition).

Analysis: calculated: C 37.97, H 6.37, N 35.43. found: C 38.1, H 6.3, N 35.4.

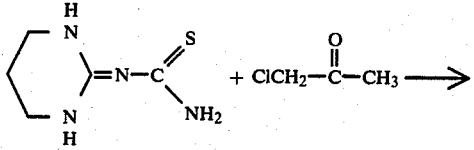

(b)       (c)

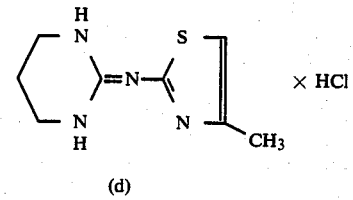

(d)

2-(N-(4'-Methylthiazol-2'-yl)imino)-hexahydropyrimidine hydrochloride (d)

A solution of 4.62 g (0.05 mol) of α-chloroacetone (c) in 20 ml of acetone is added dropwise to 7.9 g (0.05 mol) of 2-(N-thiocarbamoylimino)-hexahydropyrimidine (b) in 50 ml of acetone. The mixture is stirred at room temperature for 8 hours and left to stand overnight and the precipitate is filtered off with suction. The product is washed with acetone and then dried.

Yield: 10.4 g (90%), melting point=250°–251° C.

Analysis: calculated: C 41.29, H 5.59, Cl 15.26, N 24.08. found: C 41.1, H 5.2, Cl 15.0, N 24.2.

Compound (d) corresponds to the guanidinothiazole (9) containing alkylene bridges in Table I.

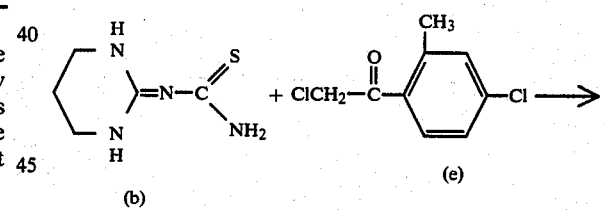

(b)       (e)

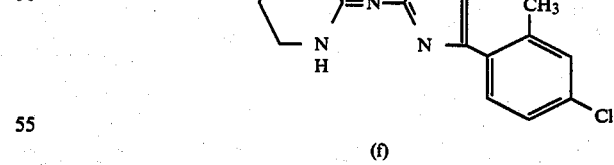

(f)

2-(N-(4'-(4"-Chloro-2"-methylphenyl)-thiazol-2'-yl)imino)-hexahydropyrimidine hydrochloride (f)

20.3 g (0.1 mol) of α,4-dichloro-2-methylacetophenone (e) are added to 15.8 g (0.1 mol) of 2-(N-thiocarbamoylimino)-hexahydropyrimidine (b) in 100 ml of acetone and the mixture is heated to the boiling point for 2 hours. A solution is obtained at the boiling point, from which the product precipitates after about 10 minutes. The reaction mixture is cooled and filtered with suction and the product is recrystallised from ethanol.

Yield: 27.7 g (81%), melting point=242°–244° C.

Analysis: calculated: C 48.98, H 4.66, Cl 20.7, N 16.33, S 9.33. found: C 49.1, H 4.8, Cl 20.4, N 16.3, S 9.4.

Compound (f) corresponds to the guanidinothiazole (33) containing alkylene bridges in Table I.

We claim:

1. A guanidinothiazole compound having an alkylene bridge, of the formula (I)

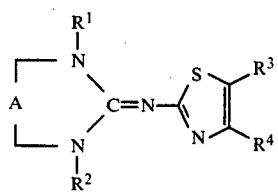

in which A represents alkylene chain having 2 to 3 carbon atoms in the chain and is optionally substituted, once or twice, by hydroxyl or alkyl with 1–4 C atoms, $R^1$ and $R^2$ are identical or different and represent hydrogen or lower alkyl, which is optionally substituted by one hydroxyl, one halogen or one acetyloxy, $R^3$ represents hydrogen, or represents carbethoxy or carbocyclohexyloxy, or represents acetyloxyethyl, p-chlorophenylcarboxamide, or methyl or phenyl, $R^4$ represents hydrogen, or represents straight-chain, or branched alkyl with 1–10 carbon atoms, or cyclo $C_3$–$C_7$ alkyl which is optionally, 1 to 3 times substituted by hydroxyl, by halogen-substituted phenyloxy or phenylthio; halogen or carboethoxy; or phenyl, biphenyl, naphthyl, tetrahydronaphthyl or indanyl, which are optionally substituted by 1 to 3 of the same or different straight or branched $C_1$–$C_{10}$ alkyl or cyclo $C_3$–$C_7$ alkyl, hydroxy, methoxy, halogen, amino or nitro; and furyl optionally substituted by nitro, and their physiological salts with acids and bases.

2. A guanidinothiazole compound of claim 1 in which $R^3$ stands for hydrogen, carboethoxy, carbocyclohexyloxy, acetyloxyethyl, p-chlorophenylcarboxamido, methyl or phenyl.

3. A compound of claim 1 wherein A is propylene; $R^1$ and $R^2$ are each hydrogen, $R^3$ is methyl and $R^4$ is

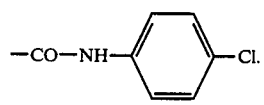

4. A compound of claim 1 wherein A is propylene; $R^1$, $R^2$ and $R^3$ are each hydrogen and $R^4$ is phenyl.

5. A compound of claim 1 wherein A is propylene; $R^1$, $R^2$ and $R^3$ are each hydrogen and $R^4$ is

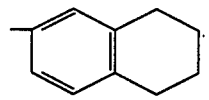

6. A compound of claim 1 wherein A is propylene; $R^1$, $R^2$ and $R^3$ are each hydrogen and $R^4$ is

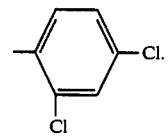

7. A compound of claim 1 wherein A is propylene; $R^1$ and $R^3$ are each hydrogen; $R^2$ is methyl and $R^4$ is

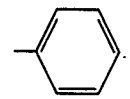

8. A pharmaceutical composition for influencing lipid metabolism comprising an effective amount of a guanidinothiazole derivative of claim 1 for influencing lipid metabolism in admixture with an inert pharmaceutical carrier.

9. A pharmaceutical composition of claim 4 in the form of a sterile or physiologically isotonic aqueous solution.

10. A composition of claim 4 having from 0.5 to 95% of said guanidinothiazole derivative by weight.

11. A medicament in dosage unit form comprising an effective amount of a guanidinothiazole derivative of claim 1 either alone or in admixture with an inert pharmaceutical carrier.

12. A medicament of claim 7 in the form of tablets, pills, dragees, capsules, ampoules or suppositories.

13. A method of influencing lipid metabolism, which comprises administering to a warm-blooded animal an effective amount of a compound of claim 1 either alone or in admixture with an inert pharmaceutical carrier or in the form of a medicament.

14. A method of claim 8 wherein the active compound is administered in an amount of 0.1 to 200 mg per kg. body weight preferred 1 to 50 mg per kg body weight.

15. A method of claim 9 wherein the active compound is administered orally.

* * * * *